United States Patent [19]

Sutherland et al.

[11] Patent Number: 4,772,727

[45] Date of Patent: Sep. 20, 1988

[54] METHOD OF PRODUCING ENANTIOMERICALLY PURE R-(+)-ALPHA-LIPOIC ACID AND S-(−)ALPHA-LIPOIC ACID (THIOCTIC ACID)

[75] Inventors: Ian O. Sutherland, Merseyside; Philip C. B. Page; Christopher M. Rayner, both of Liverpool, all of England

[73] Assignee: Degussa, Frankfurt am Main, Fed. Rep. of Germany

[21] Appl. No.: 82,567

[22] Filed: Aug. 7, 1987

[30] Foreign Application Priority Data

Aug. 27, 1986 [DE] Fed. Rep. of Germany ....... 3629116

[51] Int. Cl.4 .......................................... C07D 339/04
[52] U.S. Cl. ..................................... 549/39; 562/503; 568/31; 568/853; 568/857; 549/555
[58] Field of Search ........................... 549/39; 562/503; 568/31, 853, 857

[56] References Cited

U.S. PATENT DOCUMENTS 4,705,867 11/1987 Giray et al. ............................ 549/39

Primary Examiner—Mary C. Lee
Assistant Examiner—J. G. Mullins
Attorney, Agent, or Firm—Cushman, Darby & Cushman

[57] ABSTRACT

A multistage method for producing R-(+)-α-lipoic acid and S-(−)-α-lipoic acid (thioctic acid) by reacting a compound of formula II

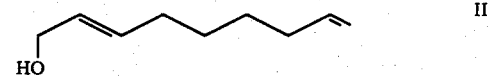

by means of enantioselective epoxidation to the epoxy alcohol of formula III,

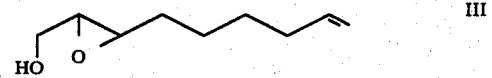

reduction to 1,3-diol-dihydroxynone-8-ene of formula IV,

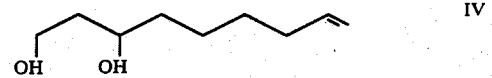

reaction with a substituted sulfonic acid chloride to 1,3-disulfoxynone-8-ene of formula V,

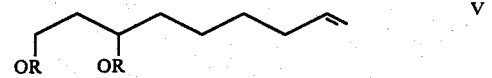

R = SO$_2$—CH$_3$, SO$_2$—C$_6$H$_4$—CH$_3$ oxidation with ruthenium tetroxide to 6,8-disulfoxyoctanoic acid of formula VI

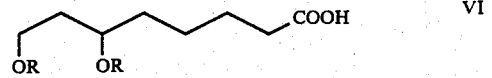

R = SO$_2$—CH$_3$, SO$_2$—C$_6$H$_4$—CH$_3$ and subsequent reaction with sodium sulfide/sulfur.

4 Claims, No Drawings

METHOD OF PRODUCING ENANTIOMERICALLY PURE R-(+)-ALPHA-LIPOIC ACID AND S-(−)ALPHA-LIPOIC ACID (THIOCTIC ACID)

The invention relates to a new method of producing enantiomerically pure 1,2-dithiolane-3-pentanoic acid (thioctic acid, α-lipoic acid) as well as certain tosyl and mesyl derivatives as intermediates for producing this acid.

BACKGROUND OF THE INVENTION

D,L-thioctic acid is used in the form of the racemic mixture as a pharmaceutical preparation for treating acute and chronic liver diseases as well as poisonings. The optically active R-(+)-α-lipoic acid is a natural substance which occurs in a slight concentration in animals and humans. R-(+)-α-lipoic acid acts as coenzyme in the oxidative decarboxylation of α-keto acids. The R-configuration of the naturally occurring α(+)-lipoic acid was confirmed by an enantioselective synthesis of the (−) antipode starting from S-malonic acid (M. H. Brookes, B. T. Golding, D. A. Howes, A. T. Hudson, "J. Chem. Soc.", Chem. Commun. 1983, p. 1051).

There are indications that the two enantiomeric forms of α-lipoic acid do not exhibit the same biological activity but rather that the S(−) enantiomer exhibits a lesser activity (J. C. Gunsalus, L. S. Barton, W. Gruber, "J. Am. Chem. Soc." 78, p. 1763, 1956). It is therefore necessary for a rational pharmaceutical therapy to use the more active enantiomeric form of α-lipoic acid. The known methods of producing α-lipoic acid yield only a racemic mixture (see DE-OS No. 35 12 911.5 and the literature cited there). A method for the resolution of racemates with D(−)arabinose is known (L. G. Chebotareva, A. M. Yurkerisch, "Khim.-Farm. Zh." 14(9), pp. 92–99, 1980; "C.A." 94 (13), 103 722 g); however, the yields achieved are only slight and the method is uneconomical.

The first known asymmetric synthesis for producing R(+)-α-lipoic acid starts from a 7-stage reaction sequence (J. D. Elliott, J. Steele, W. S. Johnson, "Tetrahedron Lett.", 1985 Vol. 26, p. 2535). Expensive chiral 2,4-pentane diol must be used as the starting material in this synthesis, so that an economical route to enantiomerically pure α-lipoic acid is not achieved. Furthermore, only one enantiomeric form can be produced.

SUMMARY OF THE INVENTION

The object of the present invention is to make available a new and economic synthesis for the production of enantiomerically pure R(+)-α-lipoic acid and S(−)-α-lipoic acid.

The synthesis starts from an achiral initial substance, so that in a later reaction step either R(+)-α-lipoic acid or S(−)-α-lipoic acid can be selectively produced by reaction with a chiral substance. The synthesis occurs in a 6-stage reaction sequence with a total yield of 22% with monitoring of the absolute configuration in the center of asymmetry on the C-6 atom of the α-lipoic acid. The products have the following formulas:

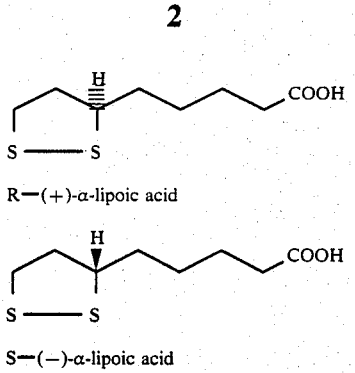

DESCRIPTION OF THE REACTION STEPS

The enantioselective synthesis uses readily accessible propargyl alcohol as the starting material. This alcohol is reacted with lithium in liquid ammonia and with 1-bromo-5-hexene in a single-vessel reaction followed by subsequent reduction with lithium of the disubstituted acetylene formed in situ to yield E-nona-2,8-diene-1-ol(II) (J. W. Patterson, "Synthesis" p. 337, 1985). The reaction sequence is shown below.

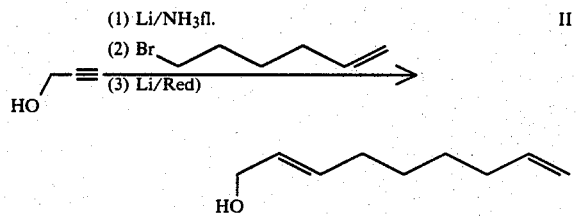

Gas capillary chromatography confirms that 100% of the product is present as E-isomer.

In the next step of the process, the E-nona-2,8-diene-1ol(II) is subjected to catalytic enantioselective epoxidation with tetraisopropyl orthotitanate and chiral tartrates, preferably with diisopropyl tartrate, and tert. butyl hydroperoxide. It is preferred to carry out this reaction in halogenated hydrocarbons, especially in methylene chloride or chloroform, at temperatures between −25° C. to −5° C. according to the method of K. B. Sharpless et al. (EP-OS No. 0 046 033; K. B. Sharpless et al., "Pure Appl. Chem." 1983, Vol. 55, p. 1823 and the literature cited there). Production of 2S, 3S-b 2-epoxy-1-hydroxynon-8-ene (III) is carried out using L(+)-diisopropyl tartrate as chiral reagent while the corresponding enantiomer 2R, 3R-2-epoxy-1-hydroxynone-8-ene is obtained with D(−)-diisopropyl tartrate.

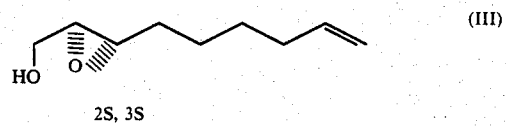

It is preferable to use 0.1 equivalents of tetraisopropyl orthotitanate, 0.12 equivalents L(+)diisopropyl tartrate, 1.2 equivalents tert. butyl hydroperoxide using methylene chloride a solvent. The catalytic amount of chiral reagent can be reduced even more when using 4 A molecular sieves (R. M. Hansons, K. B. Sharpless, "J. Org. Chem." 1922, Vol. 51, 1986).

The optical purity of the 2S, 3S-2-epoxy-1-hydroxynon-8-ene (III) with 96% e.e. can be determined by gas capillary chromatography and by $^{19}$F-NMR analysis of the ester based on the reaction with S-(−)-α-methoxy-α-trifluoromethylphenylacetyl chloride (J. A. Dale, D. L. Dull, H. S. Mosher, "J. Org. Chem." 1969, Vol. 34, p. 2543).

In the next step, the epoxy alcohol (III) is reduced with a metalorganic reducing agent such as e.g. a 1.5 to 3- fold molar excess sodium bis(2-methoxy-ethoxy)-aluminum hydride (Red-Al$^R$) in an inert organic solvent such as e.g. tetrahydrofuran or ether at temperatures of between −20° C. and +5° C. This step yields 3S-1,3-dihydroxy-non-8-ene (IV) in selective formation with the desired configuration on the C-3 atom.

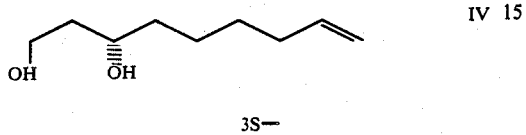

IV

3S—

The reduction occurs according to the method of J. M. Finan, Y. Kishi, "Tetrahedron Lett." 1982, Vol. 23, p. 2719.

The enantiomerically pure diol (IV) obtained in this step is converted with mesyl chloride or tosyl chloride in an inert organic solvent such as e.g. methylene chloride or chloroform at temperatures between −20° and +5° C. This leads to the 3S-dimesylate/ditosylate (V) with the desired configuration on the C-3 atom, which protects the —OH— groups in the subsequent oxidation and facilitates introducing the disulfide groups in a simple manner in a later reaction stage.

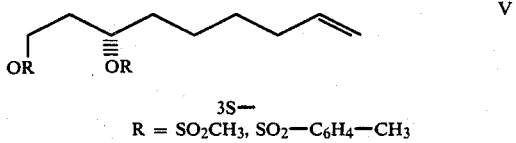

V

3S—
R = SO$_2$CH$_3$, SO$_2$—C$_6$H$_4$—CH$_3$

The formation of dimesylate or ditosylate occurs according to the general method of R. K. Crossland, K. L. Servis, "J. Org. Chem." 1970, Vol. 35, p. 3195.

The terminal double bond of this intermediate is oxidized according to the method of P. H. J. Carlsen, T. Katsuki, V. S. Martin, K. B. Sharpless, "J. Org. Chem." 1981, Vol. 46, p. 3936 with catalytic amounts (approximately 1 molar %) of ruthenium tetroxide formed in situ from ruthenium trichloride hydrate and sodium periodate. This yields 6S6,8-dimesyl/tosyl-oxyoctanoic acid (VI) with the desired center of asymmetry.

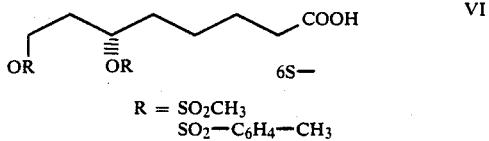

VI

6S—
R = SO$_2$CH$_3$
SO$_2$—C$_6$H$_4$—CH$_3$

A catalytic amount of ruthenium trichloride hydrate is sufficient in this reaction, while sodium periodate must be resent in a 4 to 6-fold amount in relation to the alkene (IV). The reaction medium is preferably a solvent mixture such as e.g. carbon tetrachloride, acetonitrile or chloroform.

In the next step, the two mesyl or tosyl groups are removed, and the disulfide bond is replaced in a reaction with sodium sulfide nonahydrate, sulfur and potassium hydroxide in an organic solvent such as e.g. ethanol or dimethyl formamide with inversion of the configuration on the C-6 atom and formation of the enantiomerically pure R(+)-α-lipoic acid (VII) (see M. H. Brookes, B. T. Golding, D. A. Howes, A. T. Hudson, "J. Chem. Soc.", Chem. Commun. 1983, p. 1051 and E. L. Eliel et al. "Tetrahedron Lett." 1980, p. 331). R(+)-α-lipoic acid (VII) exhibits a melting point of 44°–46° C. $[\alpha]_D^{28} = +107°$ (c=0.82 in benzene) and exhibits agreement with the literature data (melting point 43°–45° C. $[\alpha]_D^{23} = +102°$ (c=0.91 in benzene) (see J. A. D. Elliott, J. Steele, W. S. Johnson, "Tetrahedron Lett." 1985, Vol. 26, p. 2535).

The enantiomerically pure S(−)-α-lipoic acid is obtained in the same yield when using the chiral auxiliary reagent D-(−)-diisopropyl tartrate during the epoxidation to the epoxy alcohol (III).

The invention is illustrated in the following detailed description of the respective reaction steps.

EXAMPLE 1

(E)-nona-2,8-diene-1-ol (II)

100 ml liquid ammonia and a catalytic amount of ferric nitrate (5 mg) are put into a 250 ml three-neck flask which is provided with an agitator, dry-ice condenser, dropping funnel with pressure compensation and with argon/ammonia flushing. 1.88 g (0.268M) lithium is added in portions to this mixture in such a manner that the blue color disappears between the additions. 7.21 g (7.49 ml, 0.129M) propargyl alcohol is added to the reaction mixture in 20 ml dry tetrahydrofuran during 25 minutes and the mixture is allowed to react for 1.5 hours during reflux after the addition. Subsequently, 14.0 g (10.86 ml, 85.8 mM) 1-bromo-5-hexene in 30 ml dry tetrahydrofuran is added over 30 minutes and the mixture is again allowed to react under reflux for 2.5 hours. Then, 2.05 g (0.298M) lithium is added in portions to the reaction mixture and the mixture is allowed to react one more hour. Subsequently, ammonium chloride is added in such an amount that the blue color of the reaction solution disappears and the main amount of the ammonia can evaporate. The reaction mixture is subsequently put in 20 g of ice and the mixture is allowed to warm up overnight to 25° C. The reaction mixture is extracted with ether and dried over magnesium sulfate. After the solvent has been drawn off, 9.3 g (66.4 mM) E-nona-2,8-diene-1-ol is obtained by bulb tube distillation of the residue at 105° C./0.5 mm pressure. This corresponds to a yield of 78%.

Gas-chromatographic analysis confirms that pure E-isomer is present.

C$_9$H$_{16}$O: analysis calculated: C:77.09%, H: 11.50%. found: C:77.30%, H: 11.49%.

$^1$H-NMR(CDCl$_3$): δ5.90–5.50 (m,3H), δ5.05–4.90 (m,2H) δ4.07 (d,2H J=4.0 Hz) δ2.03 (s,4H) δ1.85 (br., s, 1H disappears by means of agitation with D$_2$O) δ1.40 (m,4H).

IR spectrum (film): 3350, 3090, 2915, 2860, 1675, 1640, 1460, 1440, 1230, 1090, 1000, 970, 910 cm$^{-1}$.

The bands at 1000 cm$^1$ and 970 cm$^1$ exhibit an E-substituted double bond.

EXAMPLE 2

2-epoxy-1-hydroxynon-8-ene (III)

100 ml methylene chloride is placed in a 250 ml round-bottom flask and cooled to −25° C. The reaction vessel is provided with a magnetic stirrer and a protective cover, and the reaction apparatus is flushed with protective argon gas. 2.84 g (2.97 ml, 10 mM) tetraisopropyl ortho titanate is added by a syringe into the reaction vessel; after another 5 minutes, 2.81 g (2.52 ml, 12 mM) freshly distilled L(+)-diisopropyl tartrate are added.

2.72 g (19.4 mM) (E)-nona-2,8-diene-1-ol (11) is added into the reaction mixture after another 5 minutes. Then, after yet another 5 minutes, 6.9 ml of a 3.39 molar solution in toluene (23.4 mM) of tertiary butyl hydroperoxide is added. The reaction mixture is allowed to react for 3 days at −25° C. Subsequently, the reaction vessel is put into an ice bath and 10 ml (1 ml per mM tetraisopropyl titantate added) saturated aqueous sodium sulfate solution and another 100 ml diethyl ether are added to the reaction mixture. The reaction solution is vigorously agitated for approximately 1 hour until the solution has warmed up to room temperature. The gelatinous orange-colored precipitation is separated out by means of a glass filter, washed twice with 100 ml quantities of ether and dried by suction. The solvent is evaporated from the combined filtrates and the residue is mixed with 100 ml ether and 2 ml dimethyl sulfide in order to destroy excess tertiary butyl hydroperoxide. The solution is agitated for one hour. Then, 50 ml 1 molar sodium hydroxide is added and the mixture is agitated another 3–4 hours. The ether phase is separated out, washed with 2×40 ml water, dried over magnesium sulfate and, after evaporation of the solvent in a vacuum, 2.48 g (15.9 mM) 2S, 3S-2-epoxy-1-hydroxynon-8-ene (III) is obtained by bulb tube distillation at 110° C./0.5 mm pressure. This corresponds to a yield of 82%.

The optical purity is 96% (the determination is performed by gas capillary chromatography and by $^{19}$F-NMR analysis of the ester formed in the reaction with S-(−)-α-methoxy-α-trifluoromethylphenylacetyl chloride—(see J. A. Dale, D. L. Dull, H. S. Mosher, "J. Org. Chem." 1969, Vol. 34, p. 2543), and using the chiral lanthanide shift reagent EU(hfc)$_3$ on the acetate. (R. R. Fraser, in "Asymmetric Synthesis", Ed. J. D. Morrison, Academic Press, New York, 1983, vol. 1, Chap. 9)

$C_9H_{16}O_2$: analysis calculated: C:69.19%, H:10.32%. found: C:69.19%, H:10.12%.

$^1$H-NMR (CDCl$_3$): δ5.90–5.68 (m,1H), δ5.07–4.90 (m,2H), δ3.87 (AB,1H), δ3.63 (AB,1H), δ2.92 (d, J=4 Hz, 2H), δ2.60 (br.,s,1H, disappears by exchange with D$_2$O), δ2.05 (m,2H), δ1.65–1.35 (m,6H).

IR Spectrum (Film): 3480, 3080, 2980, 2920, 2860, 1645, 1440, 1380, 1240, 1090, 1030, 995, 910, 870, 740, 720, 700 cm$^{-1}$.

EXAMPLE 3

1,3(S)-dihydroxynon-8-ene (IV)

2 ml of a 3.4 molar solution sodium bis-(2-methoxyethoxy)-aluminum hydride (Red-Al$^R$) (6.8 mM) are slowly added to a solution of 0.61 g (3.91 mM) 2S, 3S-2-epoxy-1-hydroxynon-8-ene (III) in 100 ml tetrahydrofuran at 0° C. in an argon gas atmosphere with agitation. After the addition, the mixture is allowed to react 3 hours at 0° C. and the reaction solution is subsequently left overnight at 25° C. After a careful addition of 5 ml 1 molar sodium hydroxide solution, the mixture is allowed to react one more hour with agitation. The organic phase is separated off and the aqueous phase is washed with 30 ml ether. The combined organic phases are washed with saturated sodium chloride solution, dried over magnesium sulfate and subsequently the solvent is evaporated in a vacuum. Bulb tube distillation at 130° C./0.5 mm pressure yields 0.54 g (3.42 mM) 1,3(S)-dihydroxynon-8-ene (IV) with a melting point of approximately 20° C. This corresponds to a yield of 89%.

$C_9H_{18}O_2$ analysis: calculated: C:68.31%, H:11.47%. found: C:68.02%, H:11.66%.

$^1$H-NMR( CDCl$_3$) δ5.95–5.70 (m,1H), δ5.10–4.90 (m,2H), δ4.05–3.85 (br,s,2H) disappears through agitation with D$_2$O, δ3.97–3.73 (m,3H) δ2.15–2.00 (m,2H), δ1.82–1.25 (m,8H)

IR Spectrum (film) 3360, 3100, 2940, 1640, 1470, 1440, 1420, 1380, 1330, 1200, 1090, 1040, 1000, 915, 735 cm$^{-1}$.

EXAMPLE 4

1,3(S)-dimesyloxynon-8-ene (V)

0.55 ml (7.10 mM) distilled mesyl chloride and then 1 ml (7.10 mM) distilled triethylamine are slowly added to a solution of 0.51 g (3.2 mM) 1,3(S)-dihydroxynon-8-ene (IV) in 50 ml dry methylene chloride in an atmosphere of argon gas. After 3 hours, the solvent is evaporated in a vacuum. After the addition of 50 ml ether, the solution is washed with 20 ml water, 20 ml aqueous hydrochloric acid, 10 ml water, 20 ml saturated sodium bicarbonate solution and 10 ml saturated sodium chloride solution, dried with magnesium sulfate, filtered off and then the solvent is evaporated in a vacuum. 0.97 g (3.1 mM) 1,3(S)-dimesyloxynon-8-ene (V) is obtained in a yield of 96%. The product can be used further without further purification.

$C_{11}H_{22}O_6S_2$ Analysis: calculated: C:42.02%, H:7.05%. found C:41.77%, H:7.07%.

$^1$H-NMR (CDCl$_3$) δ5.90–5.70 (m,1H) δ5.10–4.95 (m,2H) δ4.95–4.80 (quintet, J=5 Hz, 1H) δ3.35 (t, J=5 Hz, 2H) δ3.05 (s,6H) δ2.25–1.95 (m,4H) δ1.85–1.65 (m,2H) δ1.55–1.32 (m,4H).

IR Spectrum (Film): 3080, 3030, 2980, 2940, 2860, 1640, 1465, 1440, 1415, 1355, 1175, 975, 915, 825, 785, 750, 742, 735, 720, 710, 703 cm$^{-1}$.

EXAMPLE 5

6(S),8-dimesyloxyoctanoic acid (VI)

2.10 g (6.7 mM) 1,3(S)-dimesyloxynon-8-ene are placed into a reaction solution of 15 ml carbon tetrachloride, 23 ml water and 15 ml acetonitrile, and 2 crystals ruthenium trichloride hydrate and 5.87 g (27.4 mM) sodium periodate are added with vigorous agitation. The reaction mixture is agitated for 3.5 hours further at 25° C. 100 ml methylene chloride is added, the organic phase is extracted, dried over magnesium sulfate, then filtered and then the solvent is evaporated in a vacuum. 100 ml ether are added to the residue and the solution is filtered through a filter. After the evaporation of the solvent in a vacuum, 1.73 g (5.21 mM) 6(S),8-dimesyloxyoctanoic acid (VI) is obtained as a white substance with a melting point of 54°–55° C. after a recrystallization from ether.

The yield is 78%.

$C_{10}H_{20}O_8S_2$ Analysis: calculated: C:36.13%, H:6.06%. found: C:36.21%, H:6.00%.

$^1$H-NMR(CDCl$_3$) δ10.50–9.95 (br.,s,1H) disappears through shaking with D$_2$O, δ4.94–4.77 (m,1H), δ4.33 (t,J=5 Hz,2H) δ3.05 (s,6H) δ2.41 (t,J=6 Hz,2H)

δ2.44–2.30 (m,2H), δ1.83–1.55 (m,4H) δ1.55–1.30 (m,2H).

IR Spectrum (Film): 3700–2300, 3030, 2940, 2870, 1730, 1705, 1460, 1410, 1340, 1170, 1090, 970, 915, 825, 785, 735 cm$^{-1}$

EXAMPLE 6

R-(+)-α-lipoic acid (VII)

1.38 g (4.16 mM) 6(S),8-dimesyloxyoctanoic acid (VI) is dissolved in an alkaline solution of 0.23 g (4.16 mM) potassium hydroxide in 5 ml water. The water is evaporated in a vacuum under weak heating (40° C). 0.146 g (4.57 mM) flowers of sulfur and 1.10 g (4.57 mM) sodium sulfide nonahydrate are added to the residue. Then, 10 ml dimethylformamide is added to the reaction mixture and the suspension formed is heated 24 hours at 80° C. under vigorous agitation. The reaction solution is placed into 20 g ice/water, acidified with approximately 5 ml 3 molar hydrochloric acid and extracted four times with 50 ml chloroform. The solvent is evaporated in a vacuum and the residue taken into 50 ml ether. The organic phase is washed four times with 10 ml water per time, separated off, dried over magnesium sulfate and then the solvent is evaporated. The residue is extracted twice with 10 ml hot petroleum ether per time and then the solvent is evaporated in a vacuum. After recrystallization from cyclohexane, 0.44 g (2.16 mM) R(+)-α-lipoic acid is obtained in a yield of 52% in yellow leaflets with a melting point of 44°–46° C. The optical activity yields an amount of rotation of $[\alpha]_D^{28} = +107°$ (c=0.82 in benzene) (literature value: J. D. Elliott, J. Steele, W. S. Johnson, "Tetrahedron Lett.", 2535, Vol. 26, 1985; melting point: 43°–45° C. $[\alpha]_D^{23} = +102°$ (c=0.91 in benzene).

What is claimed is:

1. A method of producing R-(+-(α-lipoic acid and S-(−)-α-lipoic acid (thioctic acid) having the formula VII

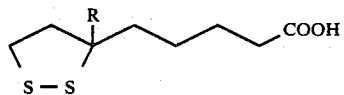

R is

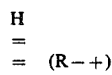

or
R is

in which
(a) a compound of formula II

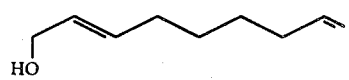

is reacted by enantioselective epoxidation to the epoxy alcohol of formula III,

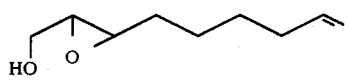

(b) reduced in a selective manner with a metalorganic reducing agent to 1,3-diol-dihydroxynon-8-ene of formula IV,

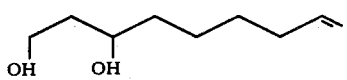

(c) 1,3-disulfoxynon-8-ene of formula V is produced with a substituted sulfonic acid chloride,

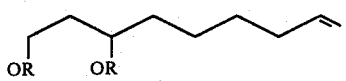

R = SO$_2$—CH$_3$, SO$_2$—C$_6$H$_4$—CH$_3$ (d) 6,8-disulfoxyoctanic acid of formula VI is produced by oxidation with ruthenium tetroxide,

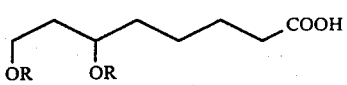
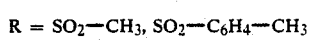

R = SO$_2$—CH$_3$, SO$_2$—C$_6$H$_4$—CH$_3$ (e) and converted by reaction with sodium sulfide/sulfur into the compound of formula VII.

2. A method according to claim 1 in which
(a) a compound of formula II is reacted by enantioselective epoxidation with tertiary butyl hydroperoxide, tetraisopropyl orthotitanate chiral tartrate in a halogenated hydrocarbon as solvent at temperatures between −25° C. and 0° C. to the epoxy alcohol of formula III,
(b) reduced in a selective manner with sodium-bis(2-methoxyethoxy)-aluminum hydride in an inert organic solvent at temperatures of −20° C. to +5° C. to 1,3-diol-dihydroxynone-8-ene of formula IV,
(c) 1,3-disulfoxynone-8-ene of formula V is produced with mesyl chloride or tosyl chloride in an inert organic solvent at temperatures between −20° C. and +5° C.,
(d) 6,8-disulfoxyoctanoic acid of formula VI is produced by oxidation with catalytic amounts of ruthenium tetroxide produced in situ in organic solvents at temperatures between 0° C. and 40° C.
(e) and converted by reaction with sodium sulfide/sulfur in an organic solvent at temperatures between 20° C. and 100° C. into the compound of formula VII.

3. 2-epoxy-1-hydroxynon-8-ene of the formula III.

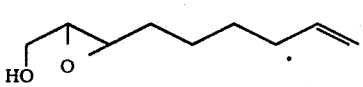

4. A method which comprises converting 2-epoxy-1-hydroxynon-8-ene of the formula III

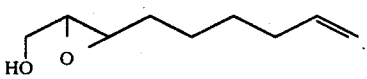

into enantiomerically pure R-(+)-/S-(−)-α-lipoic acid (thioctic acid).

* * * * *